(12) United States Patent
Adams et al.

(10) Patent No.: US 6,380,169 B1
(45) Date of Patent: Apr. 30, 2002

(54) METAL COMPLEX CONTAINING OLIGONUCLEOSIDE CLEAVAGE COMPOUNDS AND THERAPIES

(75) Inventors: Thomas H. Adams, Rancho Santa Fe; Mark A. Reynolds, San Diego, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/299,931

(22) Filed: Aug. 31, 1994

(51) Int. Cl.[7] ............................................. A01M 43/04
(52) U.S. Cl. ....................................................... 514/44
(58) Field of Search ........................... 514/44; 536/23.1, 536/24.5; 935/33, 34, 35, 37, 38, 44, 46; 435/375

(56) References Cited

U.S. PATENT DOCUMENTS 5,643,780 A * 7/1997 Baker .......................... 435/375

FOREIGN PATENT DOCUMENTS

| WO | 9110671 | * | 7/1991 | ............ C07H/1/00 |
| WO | 9117755 | * | 11/1991 | ........... A61K/31/70 |

OTHER PUBLICATIONS

J. Goodchild et al. Bioconjugate Chem. 1(3) ('90) 165–187.*
E. Uhlmann et al. Chemical Reviews 90(4) (6/'90) 543–84.*
J. Milligan et al. J. Med. Chem. 36(14) (Jul. 9, 1993) 1923–37.*
C. Stein et al. Science 261 (Aug. 20, 1993) 1004–12.*
B. Tseng et al. Cancer Gene Therapy 1(1) ('94) 65–71.*
J. Morrow et al. Inorg. Chem. 32 ('93) 3357–61.*
J. Morrow et al. J. Am. Chem. Soc. 114 ('92) 1903–5.*
P. Wessermann et al. Biomed. Biochim Ana. 48(1) ('89) 85–93.*

* cited by examiner

Primary Examiner—James Martinell
(74) Attorney, Agent, or Firm—Woodcock Washburn LLP

(57) ABSTRACT

Compositions, formulations and methods for inhibiting messenger RNA translation using anti-sense oligonucleosides containing 5'-cap cleavage moieties are described.

14 Claims, 1 Drawing Sheet

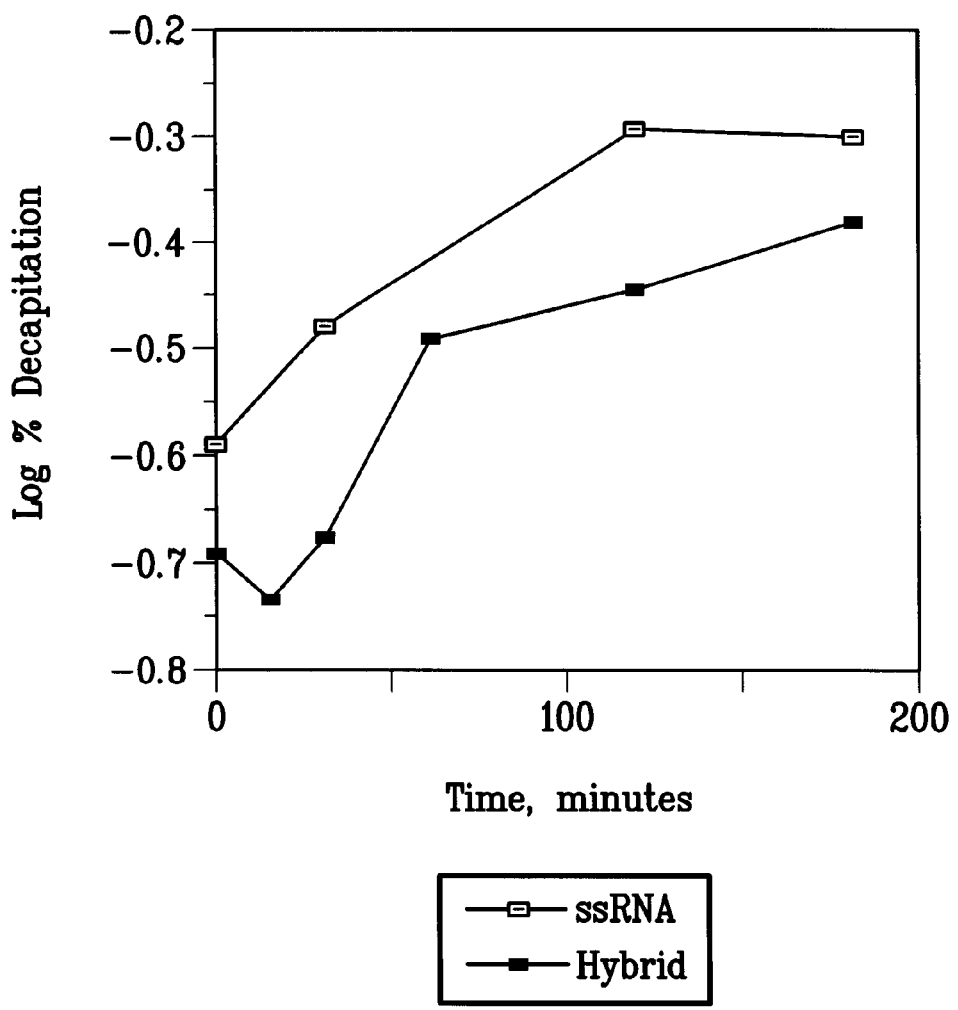
FIGURE

METAL COMPLEX CONTAINING OLIGONUCLEOSIDE CLEAVAGE COMPOUNDS AND THERAPIES

TECHNICAL FIELD

The present invention relates to the selective cleavage of a target nucleic acid using a cleavage compound. Inhibition of messenger RNA translation can be achieved using an anti-sense oligonucleoside conjugated to a cleavage-enhancing metal complex, which hybridizes to the target nucleic acid to effect cleavage at a target site in the 5'-cap structure of the nucleic acid.

BACKGROUND OF THE INVENTION

The possibility of developing therapeutic agents which bind to critical regions of RNA, for example mRNA, and selectively inhibit the function, replication or survival of abnormal cells or foreign organisms is an exciting concept. See, e.g., Dervan, *Science* 1988; 232:464–471. Various laboratories have pursued the design and development of molecules which interact with DNA in a sequence-specific manner. Such molecules have been proposed to have far-reaching implications for the diagnosis and treatment of diseases involving foreign genetic materials (such as viruses) or alterations to genomic DNA (such as cancer).

Anti-sense oligonucleotides are one type of sequence-specific molecule that has been demonstrated to be effective for inhibition of virus and human genes. In one application of this technology, anti-sense oligonucleotides are complementary to at least a portion of the messenger RNA (MRNA) transcribed from the target gene and can hybridize with the mRNA, thereby preventing ribosomal translation and subsequent protein synthesis. Anti-sense oligonucleotides have been shown to mediate inhibition of the Rous Sarcoma virus in tissue cultures (Zamecnik and Stephenson, *Proc. Natl. Sci. U.S.A.* 1978; 75:280–284) as well as the HTLV-III (HIV-1) virus (Zamecnik, et al., *Proc. Natl. Acad. Sci. U.S.A.* 1986; 83:4145–4146). Anti-sense oligonucleotides also have been shown to suppress the expression of selected non-viral genes in vitro, such as rabbit-globin (Goodchild, et al., *Arch. Biochem. Biophys.* 1988; 264:401–409) and human c-myb (Anfossi, et al., *Proc. Natl. Acad. Sci. U.S.A.* 1989; 86:3379).

Naturally-occurring oligonucleotides are subject to degradation or inactivation by cellular endogenous nucleases. Since anti-sense oligonucleotides must remain intact to be effective, some researchers have modified oligonucleotides to make them resistant to degradation or inactivation by nucleases. These modified oligonucleotides typically contain altered internucleoside linkages in which one or more of the naturally occurring phosphodiester linkages has been replaced. Oligonucleosides having phosphoroamidate or phosphorothioate linkages have been shown to increase the inhibition of HIV-1 in tissue cultures. See, e.g. Agarwal, et al., *Proc. Natl. Acad. Sci. U.S.A.* 1988; 85:7079–7083.

Nuclease-resistant nonionic oligonucleosides having methylphosphonate linkages have also been studied in vitro and in vivo as potential anticancer, antiviral and antibacterial agents. Miller, et al., Anti-Cancer Drug Design, 2:117–128 (1987). For example, anti-sense oligonucleosides containing methylphosphonate linkages have been demonstrated to inhibit HIV-induced syncytium formation. Sarin, et al., *Proc. Natl. Acad. Sci. U.S.A.* 1988; 85:7448–7451. The internucleoside bonds of these analogs are said to approximate the conformation of phosphodiester bonds in nucleic acids. It has been noted that the nucleic acid phosphate backbone in a methylphosphonate linkage is rendered neutral by methyl substitution of one anionic phosphoryl oxygen. This substitution is thought to decrease inter- and intra-strand repulsion attributable to charged phosphate groups. Miller, et al., Anti-Cancer Drug Design 2:117–128 (1987).

Oligonucleotide analogs with a methylphosphonate backbone are believed to be capable of penetrating living cells and have been reported to inhibit mRNA translation in globin synthesis and vesicular stomatitis viral protein synthesis and to inhibit herpes simplex virus replication by preventing splicing of pre-mRNA. Blake, et al., *Biochemistry* 1985; 24:6132–6138; Blake, et al., *Biochemistry* 1985; 24:6139–6145; Murakami, et al., *Biochemistry* 1985; 24:40414046; Miller, et al., *Biochimie* 1985; 67:769–776; Agris, et al., *Biochemistry* 1986; 23:6268–6275. Mechanisms of action for inhibition by the methylphosphonate analogs include formation of stable complexes with RNA and/or DNA having a substantially complementary nucleic acid sequence.

Nonionic oligonucleotide alkyl- and aryl-phosphonate analogs complementary to a selected single stranded foreign nucleic acid sequence are reported to be able to selectively inhibit the function or expression of that particular nucleic acid by binding to or interfering with that nucleic acid, without disturbing the function or expression of other nucleic acid present in the cell. See, e.g., U.S. Pat. Nos. 4,469,863 and 4,511,713. The use of complementary nuclease-resistant nonionic oligonucleoside methylphosphonates which are taken up by mammalian cells to inhibit viral protein synthesis in certain contexts, including herpes simplex virus-1, is described in U.S. Pat. No. 4,757,055.

The inhibition of infection of cells by HTLV-III by administration of oligonucleotides complementary to highly conserved regions of the HTLV-III genome necessary for HTLV-III replication and/or expression is reported in U.S. Pat. No. 4,806,463. The oligonucleotides were said to affect viral replication and/or gene expression as assayed by reverse transcriptase activity (replication) and production of viral proteins p15 and p24 (gene expression).

Anti-sense oligonucleotides or phosphorothioate or other analogs complementary to a sequence of viral RNA theoretically may be employed to interrupt the transcription and translation of viral mRNA into protein. The anti-sense constructs can bind to viral mRNA and obstruct ribosomes from moving along the mRNA, thereby halting the translation of mRNA into protein. This process is called "translation arrest" or "ribosomal-hybridization arrest." Yarochan, et al., "AIDS Therapies", Scientific American, pages 110–119 (October, 1988).

However, in practice, the use of an anti-sense hybridizing sequence to obstruct the ribosome from reading along the mRNA is not generally useful in the coding portion of the target mRNA, since an anti-sense sequence targeted to the coding portion is often removed from hybridization with the target sequence during the course of translation, even where the binding constant is high. In contrast, an anti-sense sequence targeted to the 5'-untranslated position of a mRNA molecule may achieve translation arrest through a blocking type mechanism.

One approach to selective targeting of coding sequences is to rely on the ability of RNaseH to cleave duplexed RNA strands. In theory, by utilizing an anti-sense sequence which hybridizes to a target coding sequence on RNA, RNaseH cleavage of the target RNA could be achieved in this manner. However, in practice, cleavage by RNaseH requires that the strands in the target duplex sequence have 2'-deoxy sugar portions as well as charged (e.g., phosphodiester) backbone linkages. This means that uncharged-backbone anti-sense sequences such as methylphosphonate oligonucleosides (which are particularly useful because they are less subject to in vivo degradation) would not be expected to activate RNaseH activity against target RNA sequences. As a result, the increases in potency which can be achieved using modified oligonucleosides such as the methylphosphonates may not be realized (especially with respect to coding sequence targets) if RNaseH or translation arrest is relied upon to inhibit expression.

In an effort to increase the interference with protein synthesis of target genes and thereby increase potency, various agents can be bound to the anti-sense oligonucleotides which enhance the inactivation of the target nucleic acid. Such inactivating agents include alkylating agents, crosslinking agents and cleaving agents. These agents typically are capable of chemically modifying nucleic acid nonspecifically. By linking these agents to an anti-sense oligonucleotide, the target nucleic acid may in theory be modified or altered in specific locations.

Cleaving agents which have been covalently bound to oligonucleotides include, in particular, metal complexes such as EDTA-Fe(II), o-phenanthroline-Cu(II) and porphyrin-Fe(II). Uhlmann and Peyman, Antisense Oligonucleotides: A New Therapeutic Principle, *Chem. Rev.* 1990; 90:544–585. All of these cleaving agents require special conditions to perform the cleaving function. In each case, metal ion concentration must be carefully controlled to achieve cleavage. In some cases ancillary reagents not found in vivo, such as peroxide, are required, making such agents inappropriate for in vivo use. Baker has also recently reported experiments using Cu(II)-phenanthroline and other metal ion complexes for attempted hydrolysis of 5'-capped mono- and oligoribonucleotides. Baker, B. F., *J. Am. Chem. Soc.*, 1993; 115:3378–3379.

Recently, a new class of non-site-specific nucleic acid cleaving agents has been investigated that do not require a metal ion free-radical mechanism to cleave the phosphodiester linkage. The design of these nucleic acid cleaving agents is intended to mimic the active site of naturally-occurring nucleases. Synthetic moieties modeled after nucleases such as staphylococcal nuclease have been reported to bind to phosphodiester linkages (Ariga & Ansilyn, *J. Org. Chem.* 1992; 57:417–419), as well as to accelerate both inter- and intramolecular phosphodiester cleavage (Jubian, et al., *J. Am. Chem. Soc.* 1992; 114:1120–1121). In another example, staphylococcal nuclease has been coupled to a synthetic oligonucleotide in an effort to achieve site-specific cleavage activity. Corey & Schultz, *Science* 1987; 238:1401–1403. However, this approach suffers from problems of immunogenicity, instability in biological fluids, and poor cellular uptake. Oligoamines, such as ethylenediamine, triethylenetetramine and pentaethylenehexamine, have been reported to accelerate the hydrolysis of RNA. Yoshiari, et al., Oligoamines as Simple and Efficient Catalysts for RNA Hydrolysis, *J. Am. Chem. Soc.* 1991; 113:5899–5901.

SUMMARY OF THE INVENTION

The present invention relates to the inhibition of expression of a target nucleic acid by contacting the target nucleic acid, particularly mRNA, with an oligonucleoside compound and causing selective degradation (cleavage) of the target nucleic acid. The present oligonucleoside compounds, referred to herein as "cleavage compounds," are designed to target specific nucleic acid sequences by including an oligonucleoside sequence which is substantially complementary to the 5'-terminal portion, and particularly the region containing or adjacent to the 5'-cap structure of the target mRNA. Such cleavage compounds maximize the rate of 5'-cap structure cleavage, while retaining sequence specificity, by incorporating a Lewis acid or other electrophilic or electron-withdrawing moiety, preferably a metal ion complex, at a position in the oligonucleoside compound that is proximate to the 5'-cap structure of the target mRNA once the oligonucleoside compound hybridizes to the target. Since selective cleavage of the mRNA 5'-cap structure can prevent translation into encoded protein, the present compounds and methods prevent or reduce expression of the undesired protein encoded by the responsible gene. Such cleavage compounds may be expected to yield higher potencies than compounds associated with various other approaches to translation inhibition.

The compounds of the invention are believed to act primarily or even exclusively through a Lewis acid (electron-withdrawing) mechanism wherein the Lewis acid cleavage moiety of the cleavage compound withdraws electrons from the target phosphorus-oxygen center in the triphosphate 5'-cap structure, thereby facilitating direct nucleophilic attack by in situ water or hydroxide ion to effect hydrolytic cleavage. However, the invention is not limited to this particular proposed mode of activity, and other mechanisms may be applicable.

The cleavage compounds of the invention are preferably designed to form, in the course of cleavage, a hybridized duplex structure with a single-strand target RNA. However, the compounds may also be designed to form a triple-strand structure in the course of cleavage, as for example where two cleavage compounds act in tandem to form a triple-strand structure with a single-strand target RNA.

The cleavage compounds of the invention generally include a sequence of nucleosides that is chosen to be substantially complementary to a target region of the target nucleic acid strand, specifically the 5'-region of the target mRNA containing or adjacent to the 5'-cap structure, such that the cleavage compound is capable of hybridizing in a double-strand or triple-strand fashion to the 5'-region of target nucleic acid to effect cleavage of the cap structure. The "substantially complementary" portion is chosen so as to provide suitable target specificity and binding affinity of the cleavage compound. Oligonucleosides of the present invention are preferably between about 6 to 40 nucleosides in length, more preferably between 12 to 30 nucleosides. The length of a particular cleavage compound, the number of complementary bases in the compound, and the identity and location of the complementary bases may be adapted so that suitable target specificity and binding affinity will be achieved under the conditions in which the compound will be used. These conditions include, for example, the effective concentration of the cleavage compound inside the cell, the concentration and turnover rate of the target sequence, the desired level of reduction of concentration of the target sequence, the efficacy of cleavage, and the mode of cleavage (e.g., catalytic or non-catalytic).

The present oligonucleoside cleavage compounds preferably are modified to render them resistant to degradation by cellular nucleases or other enzymes that are present in vivo. This modification can be accomplished by methods known in the art, e.g., by incorporating one or more internal artificial internucleoside linkages, such as by modifying the phosphodiester linkage to include alternate or additional groups in conjunction with a phosphorus atom (e.g., by replacing one of the non-bridging phosphate oxygens in the linkage with sulfur or other atoms), and/or by blocking the 3' end of the oligonucleoside with a capping structure. Likewise, the Lewis acid cleavage moiety portion can be conjugated to the cleavage compound using similar attachment chemistry, or using other techniques as described below. Multiple cleavage moieties can be conjugated to a single cleavage compound if desired, for example to increase the electrophilic cleavage-enhancing effect at the 5'-cap site.

Several advantages are provided by the cleavage compounds according to the present invention. The present compounds are target-mRNA-specific by virtue of their complementary oligonucleotide character, and therefore can be used against mRNA specific to a particular disease state. The cleavage agents are believed to facilitate hydrolysis by enhancing attack by an in situ nucleophilic species (especially water or hydroxide ion) on a phosphate ester bond of the triphosphate 5'-cap region of a target RNA sequence, and no free-radical mechanism utilizing metal ions or other compounds is required to implement the cleavage of the target RNA, making in vivo applications possible. Since the hydrolysis is performed by nucleophilic attack, rather than by hydroxyl free-radical attack as is common with some metal ion complexes, only the desired cleavage site should be hydrolyzed by the present compounds. Further, eliminating the creation of free radicals by the cleaving agent also allows in vivo use, as the present compounds are expected to be relatively harmless to non-targeted nucleic acid. The present compounds in some instances may also be catalytic in nature, permitting the administration of a relatively small amount of the present compounds for treatment.

Another feature of the present invention is the administration of the cleavage compounds described herein to treat diseases or other conditions characterized by the presence of undesired nucleic acid. The methods of the present invention are useful for inhibiting the expression of protein encoding genes. Administration of the present cleavage compounds can be accomplished by methods known in the art, such as systemic, topical or localized administration. Preferably, the present cleavage compounds are administered in an amount sufficient to prevent or reduce the normal translation of the target nucleic acid.

Other features and advantages of the present invention will be apparent upon review of the detailed description of the preferred embodiment, the drawings and the claims.

BRIEF DESCRIPTION OF THE DRAWING

FIG. 1 is a graph showing the rate of cleavage of a 5'-capped RNA single strand substrate, and of the same substrate hybridized to a complementary DNA oligomer, in the presence of Eu[THED]$^{3+}$.

DEFINITIONS

As used herein, the following terms have the following meanings unless otherwise indicated.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-5-donor/acceptor bases such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "nucleotide" refers to a subunit of a nucleic acid which consists of a nucleoside plus a phosphate group.

The term "purine" or "purine base" includes not only the naturally occurring adenine and guanine bases, but also modifications of those bases, such as bases substituted at the 8-position, or guanine analogs modified at the 6-position or the analog of adenine, 2-amino purine, as well as analogs of purines having carbon replacing nitrogen at the 9-position, such as the 9-deaza purine derivatives and other purine analogs.

The term "phosphonate" refers to the group

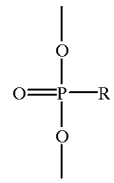

wherein R is hydrogen or an alkyl or aryl group. Suitable alkyl or aryl groups include those which do not sterically hinder the phosphonate linkage or interact with each other. The phosphonate group may exist in either an "R" or an "S" configuration. Phosphonate groups may be used as internucleosidyl phosphorous group linkages (or links) to connect nucleosidyl units.

The term "phosphodiester" or "diester" refers to the group

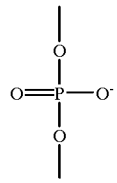

wherein such phosphodiester groups may be used as internucleosidyl group linkages (or links) to connect nucleosidyl units.

A "non-nucleoside unit" refers to a monomeric unit wherein the base, the sugar and/or the phosphate backbone or other internucleosidyl linkage group of a nucleoside has been replaced by some other chemical moiety(s).

A "nucleoside/non-nucleoside polymer" refers to a polymer comprised of nucleoside and non-nucleoside monomeric units.

The term "oligonucleoside" refers to a chain of nucleosides, optionally containing one or more non-nucleoside units, which are linked by internucleoside linkages. Such a chain is generally from about 4 to about 100 nucleosides in length, but which may be greater than about 100 nucleosides in length. It may be synthesized from nucleoside monomers or may also be obtained by enzymatic means. Thus, the term oligonucleoside refers to a chain of nucleosides which have internucleosidyl linkages linking the nucleoside monomers and, thus, includes oligonucleotides; nonionic alkyl- and aryl-phosphonate oligonucleotide analogs; alkyl- and aryl-phosphonothioate, phosphorothioate and phosphorodithioate oligonucleotide analogs; phosphoroamidate oligonucleotide analogs; neutral phosphate ester oligonucleotide analogs, such as phosphotriesters; and other analogs and modified forms of linked nucleosides, including nucleoside/non-nucleoside polymers. The term also includes linked nucleosides and nucleoside/non-nucleoside polymers wherein one or more of the phosphorus group linkages between monomeric units has been replaced by a non-phosphorus linkage such as a formacetal linkage, a thioformacetal linkage, a sulfamate linkage, or a carbamate linkage. The term also includes nucleoside/non-nucleoside polymers wherein both the sugar and the phosphorus moiety of one or more monomeric units have been replaced or modified such as with morpholino base analogs, or polyamide base analogs. The term also includes nucleoside/non-nucleoside polymers wherein the base, the sugar, and the phosphate backbone of one or more monomeric units are replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells. The term also includes nucleoside/non-nucleoside polymers wherein a non-complementary portion and/or a cleavage moiety portion, as described herein, are inserted into the polymer.

The term "alkyl- or aryl-phosphonate oligonucleoside" refers to oligonucleosides having at least one alkyl- or aryl-phosphonate internucleosidyl linkage. Suitable alkyl- or aryl-phosphonate groups include alkyl- or aryl-groups which do not sterically hinder the phosphonate linkage or interact with each other. Preferred alkyl groups include lower alkyl groups having 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate oligonucleoside" refers to oligonucleosides having at least one methylphosphonate internucleosidyl linkage.

The term "neutral oligonucleoside" refers to oligonucleosides which have nonionic internucleosidyl linkages between nucleoside monomers (i.e., linkages having no positive or negative ionic charge) and include, for example, oligonucleosides having internucleosidyl linkages such as alkyl- or aryl-phosphonate linkages; alkyl- or aryl-phosphonothioate linkages; neutral phosphate ester linkages such as phosphotriester linkages, especially neutral ethyltriester linkages; and neutral non-phosphorus containing internucleosidyl linkages, such as sulfamate, morpholino, formacetal, thioformacetal, and carbamate linkages. Optionally, a neutral oligonucleoside may comprise a conjugate between an oligonucleoside (including a nucleoside/non-nucleoside polymer) and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the oligonucleoside, modify the interaction or the oligonucleoside with the target sequence, or alter the pharmacokinetic distribution of the oligonucleoside. The essential requirement is that the oligonucleoside comprised by the oligonucleoside conjugate be substantially neutral.

The term "substantially neutral" in referring to an oligonucleoside refers to those oligonucleosides in which at least about 80 percent of the internucleosidyl linkages between the nucleoside monomers are nonionic linkages.

The term "neutral alkyl- or aryl-phosphonate oligonucleoside" refers to neutral oligonucleosides having neutral internucleosidyl linkages which comprise at least one alkyl- or aryl-phosphonate linkage.

The term "neutral methylphosphonate oligonucleoside" refers to neutral oligonucleosides having internucleosidyl linkages which comprise at least one methylphosphonate linkage.

The term "complementary" refers to oligonucleosides (or nucleoside units therein), especially anti-sense sequences, having a nucleoside sequence (or a base portion) which is capable of forming hydrogen bonds, and thereby base pairing or hybridizing, with the base sequence of a region of the target nucleic acid to form a Watson-Crick or "double helix" type structure (whether or not actually helicized) or a portion thereof.

The term "substantially complementary" refers to oligonucleosides which may lack a complement for one or more nucleotides in the target region or subregion, but which still have sufficient binding affinity for the target sequence to form a hybridized, double helix type structure within the subject (e.g., in vivo) environment, so as to specifically recognize the target sequence and promote cleavage as described herein. The term also embraces oligonucleosides, or pairs of distinct oligonucleosides which have sufficient complementarity to achieve triple-strand binding with a target nucleic acid single-strand sequence in the subject environment, thereby to promote cleavage as described herein.

DETAILED DESCRIPTION OF THE PREFERRED EMBODIMENT

According to the present invention, methods and compounds for inhibiting the undesired expression of genes are described. Specifically, strategies are described for preparing oligonucleoside cleavage compounds that are specific to the 5'-terminal region of a target mRNA or pre-mRNA, particularly the region containing or adjacent to the 5'-cap structure, and which facilitate the hydrolysis or other cleavage 5'-cap structure of the target nucleic acid. Also described are preferred methods for administering oligonucleoside cleavage compounds prepared according to the present invention to treat diseases or conditions associated with the undesired expression of a target nucleic acid.

More particularly, the invention includes oligonucleoside compounds for hybridizing to a target nucleic acid strand, comprising an oligonucleoside sequence that is substantially complementary to the 5'-terminal region of the target nucleic acid strand, and a cleavage moiety, the cleavage moiety comprising a Lewis acid or other electron-withdrawing group, most preferably a complexed, e.g., chelated, metal ion. Particularly preferred are complexed or chelated lanthanide ions, especially the europium (III) complex of 1,4,7,10-tetrakis (2-hydroxyethyl)-1,4,7,10-tetraazacyclododecane (Eu[THED]).

Specifically, the invention includes oligonucleoside cleavage compounds for hybridizing to the 5'-terminal region of a target mRNA nucleic acid strand and effecting cleavage thereof, comprising an oligonucleoside sequence that is substantially complementary to the 5'-terminal region of the target nucleic acid strand, and a metal complex containing cleavage moiety conjugated at a position in the cleavage compound that is proximate to the 5'-cap structure of the target strand upon hybridization, such that the cleavage moiety is capable of effecting cleavage of the 5'-cap structure of the target strand.

The present invention also provides methods for inhibiting production of a selected protein (or peptide) in a cell or by a multicellular organism (such as a mammal), comprising administering to the cell or organism a cleavage compound as described herein in an amount effective to effect cleavage at the 5'-cap structure of the RNA that codes for the selected protein. Conditions caused by the production of the selected protein or peptide may thereby be therapeutically treated, or the effects of such cleavage and inhibition may be studied in in vitro or ex vivo environments.

A. Preferred Complementary Oligonucleoside Structures

The therapeutic approach and the cleavage compounds of the present invention are based on the principle that the function of a gene can be disrupted by preventing or inhibiting expression of the protein or other product encoded by that gene. In principle, protein synthesis disruption can be accomplished by providing an oligonucleoside of appropriate structure and length which is complementary to at least a portion of the messenger RNA (mRNA) transcribed from the target gene. Such complementary sequences are commonly called "anti-sense" compounds. In the present invention, the anti-sense oligonucleoside cleavage compound hybridizes to the target mRNA in the intracellular environment in proximity to the 5'-cap structure of the target mRNA and inactivates the mRNA by cleaving the cap structure, thereby preventing ribosomal translation and resultant protein synthesis.

The oligonucleoside cleavage compounds of the invention will typically have a sequence that is complementary to a target region at the 5'-terminus of the target nucleic acid. However, absolute base-by-base complementarity is not normally required. Any oligonucleoside having sufficient complementarity to form a stable and target-specific duplex or triplex hybrid with the target nucleic acid in the subject environment, and thereby being capable of effecting cleavage, is "substantially complementary" and is considered to be suitable.

Efficacy of hybridization is related to the strength of the hydrogen bonding between corresponding bases as well as the specificity of the cleavage compound to the complementary target nucleic acid. The specificity of anti-sense oligonucleosides arises from the formation of Watson-Crick base pairing between the heterocyclic bases of the oligonucleoside and spatially-proximate complementary bases on the target nucleic acid. The strength of the hydrogen bonding is influenced by the number and percentage of bases in an anti-sense oligonucleoside cleavage compound that are base-paired to complementary bases on the target sequence, according to Watson-Crick base pairing. To be specific for the target nucleic acid strand, the complementary bases of the anti-sense cleavage compound must be sufficient in number as to avoid non-specific binding to other non-target sequences within the mRNA population, and at the same time small enough in number to avoid non-specific binding between a subportion of the oligonucleoside cleavage compound and non-target sequences.

For example, based on statistical considerations alone, a given nucleotide sequence 12 nucleotides in length will be expected to occur randomly only once every $4^{12}$, or about $2 \times 10^7$, nucleotides. Accordingly, such a 12-nucleotide sequence is expected to occur only once among the population of mRNA molecules transcribed by the human genome. In contrast, a nucleotide sequence 6 nucleotides in length might occur randomly every $4^6$, or 4096, nucleotides. Such a sequence might be present thousands of times among the population of transcribed RNA molecules in humans. Consequently, and within the limitations expressed above, complementary oligonucleosides of greater length (and having a defined sequence) are generally more specific than oligonucleosides of lesser length and are generally less likely to induce toxic complications that might result from unwanted hybridization and cleavage.

However, other factors will also influence the choice of oligonucleoside length that is optimum for a given cleavage application. These factors include the binding affinity of the cleavage compound for the particular target nucleic acid sequence, which will influence the stability and lifetime of the hybrid structure, and in turn the kinetics of cleavage; the concentration of cleavage compound that can safely and practically be achieved inside the cell, given considerations such as the cellular uptake rate, the degradation rate and the clearance rate for the cleavage compound; the concentration and turnover rate of the target nucleic acid sequence, and the influence of various biological processes such as the processional rate of the ribosome along the mRNA-target, the level of reduction of concentration of the target sequence that is sought to be achieved; the efficacy and mode of cleavage (e.g., catalytic or non-catalytic); and other related factors.

Given the teachings of the present disclosure, those skilled in the art will be able to ascertain optimum oligonucleoside lengths, and suitable complementary sequences, to achieve structures that are substantially complementary to the desired target sequences and that have suitable potency. In general, oligonucleosides of about 6 to about 40 nucleosidyl units in length which have sufficient complementarity to form a double helix type structure having a melting temperature ($T_m$) of greater than about 40° C. under physiological conditions are particularly suitable for use according to the methods of the present invention. Preferably, the cleavage compounds of the invention each comprise from about 12 to about 30 nucleosides.

The complementary oligonucleoside sequence of the present cleavage compounds may be selected based on analysis of the sequence of the gene to be inhibited, by analysis of mRNA transcribed from that gene (as by analysis of cDNA reversed transcribed from such mRNA), by analysis of the amino acid sequence of the translated polypeptide product, or by other methods. The gene sequence can be determined, for example, by isolation and sequencing, or if known, through the literature.

The oligonucleoside selected may be any of a number of types, including those having charged or uncharged internucleosidyl bonding groups in the "backbone" of the sequence. Preferred oligonucleosides include alkyl- or arylphosphonates with methylphosphonates being especially preferred. Other preferred oligonucleosides include phosphorothioates, morpholino analogs, formacetal analogs and peptide nucleic acid ("PNA") analogs, and mixtures of such analogs in a single oligonucleoside compound.

Oligonucleosides having the desired internucleoside linkages may be conveniently prepared according to synthetic techniques known to those skilled in the art. For example, commercial machines, reagents and protocols are available for the synthesis of oligonucleosides having phosphodiester and certain other phosphorus-containing internucleoside linkages. See also Gait, M. J., *Oligonucleotide Synthesis: A Practical Approach* (IRL Press, 1984); Cohen, Jack S., *Oligodeoxynucleotides Anti-sense Inhibitors of Gene Expression*, (CRC Press, Boca Raton, Fla., 1989); and *Oligonucleotides and Analogues: A Practical Approach* (F. Eckstein, 1991); Agrawal, S. (ed.), *Protocols for Oligonucleosides and Analogs, Methods in Molecular Biology*, Vol. 20 (Humana Press, Totowa N.J. 1993).

Preparation of oligonucleosides having certain non-phosphorus-containing internucleotide linkages is described in U.S. Pat. No. 5,142,047, the disclosure of which is incorporated herein by reference. More particularly, synthetic methods for preparing methylphosphonate oligonucleosides are described in Agrawal, above, Chapter 7, pages 143–164 (Hogrefe, R. I.), and in published PCT applications WO 92/07864 and WO 92/07882, the disclosures of which are incorporated herein by reference. Particular methods for preparing representative oligonucleosides for cleavage purposes are described in examples given below.

Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target. See, for example, U.S. patent application Ser. No. 08/068,140 and WO 92/02532.

In one preferred aspect of the invention, chirally pure oligonucleosides are used. Alternatively, oligonucleosides comprising at least one chirally pure internucleosidyl linkage may be used and may be preferred. Such oligonucleosides, for example with methylphosphonate or phosphorothioate linkages, may be prepared using methods as those described in Lesnikowski, et al., *Nucleic Acids Research* 1990; 18(8):2109–2115 and Stec, et al., *Nucleic Acids Research* 1991; 19(21):5883–5888. Preferably, the methods described in copending U.S. patent application Ser. Nos. 08/154,013 and 08/154,014 may be employed.

Suitable oligonucleosides also include chimeric oligonucleotides which are mixed RNA, DNA analogs (Perreault, et al., *Nature* 1990; 344:565–567). Other suitable oligonucleosides include those having chimeric backbones. Such backbones may include a mixture of internucleosidyl linkages which may or may not include phosphorus atoms, such as morpholinyl linkages, formacetal linkages, peptide nucleic acid (PNA) linkages and the like. Oligonucleosides having a neutral backbone, for example methylphosphonate oligonucleosides may have a longer half-life in vivo since the neutral structure reduces the rate of nuclease digestion.

B. Preferred Metal Complex Containing Cleavage Moiety Portions

The 5'-cap structure found in eukaryotic and viral mRNAs consists of a modified, reversed-orientation (3'-5') purine triphosphate structure (e.g., $N^7$-methylguanosine triphosphate, $m^7$Gppp) which acts (a) to stabilize the mRNA against degradation by endogenous nucleases, (b) to facilitate translation by promoting ribosome-mRNA binding, (c) to assist in message processing and maturation (e.g., slicing), and (d) to facilitate message transport from the nucleus to the cytoplasm. See, e.g., Darzynkiewicz, et al., *Nucl. Acids Res.*, 1988; 16(18):8953–8962; Pelletier and Sonenberg, *Biochem. Cell. Biol.*, 1987; 65:576–581; Ohno, et al., *Proc. Natl. Acad. Sci. USA,* 1987; 84:5187–5191; Shatkin, *Cell,* 1976; 9:645–653. The present compounds are capable of cleaving one or more phosphate ester bonds of the triphosphate 5'-cap structure and thus can be expected to inhibit or eliminate translation both by eliminating the translation-enhancement effects of the cap structure and by exposing the mRNA to further degradation by endogenous exonucleases.

The present cleavage compounds include compounds that incorporate a non-nucleoside or modified nucleoside cleavage moiety at a position which, when the cleavage compound is hybridized to the target sequence, is sufficiently proximate to the 5'-cap structure of the target nucleic acid as to promote cleavage of one or more of its internal phosphate linkages. The cleavage moiety may be incorporated into the cleavage compound using a linker group which attaches the cleavage moiety to the remainder of the cleavage compound. Thus, the cleavage moiety may be appended via a nucleoside base linker group (e.g., a modified cytidine or guanosine base), or via a non-base linker group (e.g., an intercalator or linker-arm, for example amide or ester-based hydrocarbon chain linker arms) at a position in the cleavage compound that is positionally complementary to the 5'-cap structure. Alternatively, the cleavage moiety may be appended at a position in the cleavage compound that is separated by one or more nucleosidyl units from the phosphate bond in the cap structure that is to be cleaved, in which case the appendage point of the cleavage moiety will not be positionally complementary to the targeted bond. In either case, the linker group connecting the cleavage moiety to the remainder of the cleavage compound will have a size and conformation that allows the cleavage moiety to assume a position that is proximate to the bond (or bonds) targeted for cleavage when the cleavage compound is hybridized to the target nucleic acid sequence.

Chemical synthesis methods and linker groups for conjugating the cleavage moiety to the cleavage compound are available in the art. In general, the techniques for linking cleavage moieties may be similar to known techniques for linking labels or other groups to functional groups on proteins. See, e.g., G. M. Means and R. E. Feeney, *Chemical Modifications of Proteins* (Holden-Day Inc., 1971); R. E. Feeney, *Int. J. Peptide Protein Res.* 1987; 29:145–161. Preferably, the methods of copending U.S. patent application Ser. No. 08/068,140 (filed May 26, 1993) and Publication No. WO92/02532 (for example, the "C2" non-nucleoside bridging/linking group described therein) may be employed. Linker arms having a suitable length (e.g., hydrocarbon chain linker arms) can readily be selected given the present teachings. Examples of such linker arms include polyfunctional hydrocarbon chain structures which can be attached to a hydroxyl, carboxylate, amino or methylene group of a metal chelator (e.g., a macrocylic complexing agent) using ester, amide or other attachment chemistry. Attachment of the cleavage moiety may be achieved using coupling reactions known in the art, as for example by reacting an amine (e.g., alkylamine) group with a reactive ester, imine, aldehyde, acid halide, aryl halide, epoxide, aziridine, (iso)thiocyanate or sulfonyl moiety; or reacting a thiol group with a reactive haloacetyl, haloacetamide, disulfide, maleimide, arylmercury or sulfonyl moiety; or reacting a hydroxyl group with a reactive acid halide, ester, epoxide, aziridine or sulfonyl moiety. Suitable protecting groups will generally be employed to protect the other cleavage-enhancing groups on the cleavage moiety, or other reactive groups, during coupling (see, for example, E. Gross and J. Meienhofer (eds.), *The Peptides: Analysis and Synthesis, Biology*, Vol. 3 (Academic Press, 1971)). Other methods will be discernable given the teachings of the present disclosure.

The cleavage moiety may be located internally within the overall oligonucleoside sequence of the cleavage compound, or, preferably, it may be located at or near the 3'-terminal position of the compound that will be proximate to the 5'-cap structure of the target strand upon hybridization of the cleavage compound to the target strand. Thus, target-specific cleavage of a 5'-cap structure can be achieved by conjugating the Lewis acid cleavage moiety at or near the 3'-terminus of an oligonucleoside sequence that is substantially complementary to the 5'-terminal region of the target mRNA. For example, the cleavage moiety can be linked to the 3'-terminus of the cleavage compound or it may be linked to the penultimate unit of the cleavage compound with the 3'-terminal nucleoside being a pyrimidine that is complementary to the 5'-terminal purine of the target 5'-cap structure. Still further, multiple oligonucleoside compounds may be used in tandem, as for example where one anti-sense oligonucleoside hybridizes to the 5'-terminal region of the target strand and also has an extra 3'-extended portion which (following hybridization of the first oligonucleoside to the target strand) extends freely so as to hybridize with a separate cleavage compound that is complementary to the 3'-extended portion and that contains a cleavage moiety at or near its 3'-terminus. In this case, the cleavage moiety of the cleavage compound will be in proximity to the 5'-cap structure following hybridization to the first oligonucleoside. Furthermore, multiple cleavage moieties can be employed in a single cleavage compound to enhance the cleavage effect.

The cleavage compounds of the invention preferably utilize a metal complex containing Lewis acid or electrophilic cleavage moiety which serves to activate the phosphate center of the target 5'-cap triphosphate by strong electron-withdrawing effects. The mechanism of activity of this approach is believed to involve direct hydrolytic attack by in situ water or hydroxide ion on the activated phosphate center.

Complexed (e.g., chelated) metal ion moieties are preferred, such as chelated zinc or other moieties that can effect cleavage by electron-withdrawing effects (as distinct from a free-radical mechanism of activity). Likewise, other metal ions, such as lanthanides, or bimetallic structures (see Steitz & Steitz, *Proc. Natl. Acad. Sci. USA* 1993; 90:6498–6502), may be used. Macrocyclic complexing agents are preferred, particularly polyfunctional macrocyclic complexing agents that include nitrogen, oxygen (e.g., hydroxyl) or other electron-rich coordination sites. Especially preferred are macrocyclic chelated trivalent lanthanide ions such as the europium (III) complex of 1,4,7,10-tetrakis(2-hydroxyethyl)-1,4,7,10-tetraazacyclododecane (Eu[THED]), as described in Morrow and Chin, *Inorg. Chem.*, 1993; 32:3357–3361 (which is hereby incorporated by reference) and below.

Factors to be considered in conjugating a Lewis acid cleavage moiety to a target-complementary oligonucleoside include the site of attachment of the chelate on the oligonucleoside, the type of chemistry used to covalently attach the Lewis acid cleavage moiety such that the modified oligonucleoside does not affect the hydridization of the probe to the target, the type of Lewis acid cleavage moiety, and the sequence of the oligonucleoside. It is preferable, as mentioned above, to conjugate the Lewis acid cleavage moiety to the 3'-terminus of the target-complementary oligonucleoside. Various chemistries can be used to covalently attach a moiety to a biological molecule, and those skilled in the art of bioconjugation chemistry will recognize suitable approaches in view of the teachings of the present disclosure. See, for example, Conjugates of Oligonucleotides and Modified Oligonucleotides: A Review of their Synthesis and Properties, J. Goodwin, Bioconjugate Chem 1, 165 (1990) and Chemical Modifications of Proteins: History and Applications, G. E. Means and R. E. Feeney, Bioconjugate Chemistry 1, 2 (1990), the disclosures of which are incorporated herein by reference.

C. Therapeutic Uses

Many diseases and other conditions in multicellular organisms, particularly mammals including humans, are characterized by the presence of undesired DNA or RNA, which may in certain instances be in single-stranded form and in other instances in double-stranded form. These diseases and conditions can be treated using the principles of anti-sense therapy as is generally understood in the art.

According to the methods of the present invention, a hybrid complex is formed having a sufficiently high degree of selectivity and affinity as to interact with the target strand of interest. The cleavage compounds may be used to detect or locate and then irreversibly modify the target site in the nucleic acid by cleaving the 5'-cap structure.

The oligonucleotide compounds may be administered in any convenient vehicle that is physiologically acceptable. In therapeutic applications, the cleavage compounds can be formulated for a variety of modes of administration, including systemic, topical or localized administration. Techniques and formulations generally may be found in *Remington's Pharmaceutical Sciences*, Mack Publishing Co., Easton, Pa., latest edition. In each case, a therapeutic amount of the cleavage compound is administered when the normal translation of the target nucleic acid is to be prevented. The cleavage compound is generally combined with a carrier such as a diluent or excipient which may include fillers, extenders, binding, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection may be preferred, including intramuscular, intravenous, intraperitoneal, and subcutaneous. For injection, the cleavage compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some instances, the compositions may be infused upstream from the site of the cells whose activity is to be modulated. The localized concentration or amount administered may be determined empirically and will depend upon the purpose of the administration, the area to be treated, the effectiveness of the composition, and the manner of administration. The localized concentration will desirably be in the range of about 1 to 50 $\mu$M, or lower if appropriate.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, as well as formulations suitable for administration by inhalation, or suppositories. For oral administration, the oligonucleosides are formulated into conventional as well as delayed release oral administration forms such as capsules, tablets, and tonics.

For topical administration, the oligonucleosides for use in the invention are formulated into ointments, salves, eye drops, gels, or creams, as is generally known in the art.

The following examples are included by way of illustration and are not intended to limit the scope of the invention.

EXAMPLE 1

Cleavage of $m^7$GpppG cap Structure by Metal Complex Containing Hydrolytic Catalysts The present example establishes that certain lanthanide containing metal complex cleavage moieties are useful in hydrolyzing 5'-cap structures associated with mammalian mRNA and pre-mRNA. The model substrate m⁷GpppG was used in these studies:

$C_{19}H_{36}N_4O_{13}F_9S_3Eu$: C, 24.10; H, 3.80, N, 5.91;Eu, 16.05. Found: C, 23.82; H, 3.82; N, 5.79; Eu, 16.29. FABMS (m/z): 798 $(Eu(THED)(CF_3SO_3)_3—CF_3SO_3)$. ¹H NMR (d⁴-

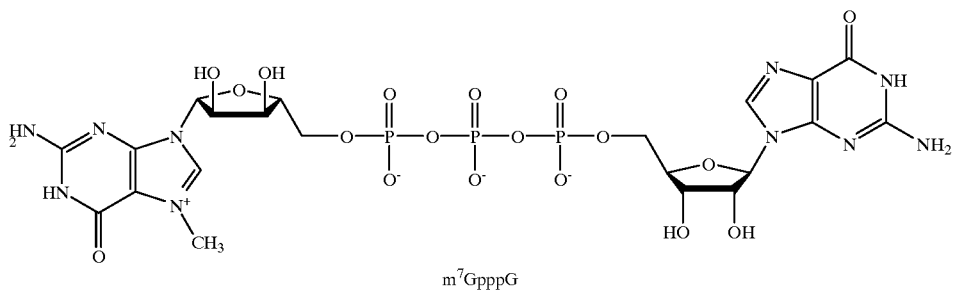

m⁷GpppG

The m⁷GpppG substrate was purchased from Pharmacia LKB (Piscataway, N.J.). Guanosine 5'-monophosphate (GMP), 7-methylguanosine 5'-monophosphate (m⁷GMP), guanosine 5'-diphosphate (GDP), and guanosine 5'-triphosphate (GTP) were purchased from Sigma Chemical Company (St. Louis, Mo.). Ethylenediamine (EDA) was purchased from Fisher Scientific, redistilled under argon and stored at −20° C. prior to use. Europium complexes of [1,4,7,10-(2-hydroxyethyl)]-1,4,7,10-tetraazocyclododecane (Eu[THED]) and [1,4,7,10-(S-2-hydroxypropyl)]-1,4,7,10-tetraazocyclododecane (Eu[S-THP]) were provided by Janet Morrow at the State University of New York (Buffalo, N.Y.).

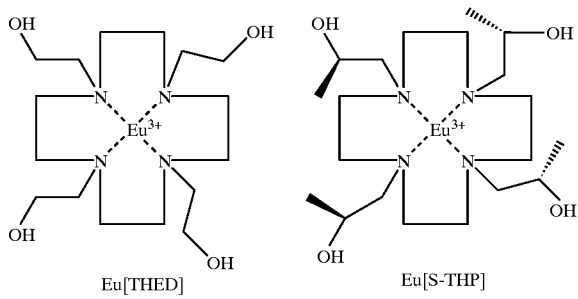

Eu[THED]  Eu[S-THP]

The europium (III) complex of 1,4,7,10-tetrakis (2-hydroxyethyl)-1,4,7,10-tetraazacyclododecane (Eu [THED]), for example, may be prepared using procedures similar to those employed for the synthesis of the lanthanide (III) cryptates (e.g., Gansow, et al., *J. Amer. Chem. Soc.* 1977; 99:7087–7089; Ciampolini, et al., *J. Chem. Soc.* (Dalton Trans.), 1979; 1979:974–977). The EU[THED] compound of the present example was prepared by treating $Eu(CF_3SO_3)_3$ with the free-base form of THED to yield the complex in good yield, as described in Morrow and Chin, *Inorg. Chem.*, 1993; 32:3357–3361. The use of anhydrous conditions is necessary to avoid the production of lanthanide hydroxide precipitates. Typically, $Eu(SO_3CF_3)_3$ (one equivalent, e.g. about $5.75 \times 10_{-4}$ mol) was refluxed under nitrogen in a mixture of about 50 mL of dry acetonitrile and about 5.6 mL of trimethyl orthoformate for several hours. THED (one equivalent, e.g. about $5.75 \times 10_{-4}$ mol) dissolved in acetonitrile was introduced by cannula into the solution containing europium. The mixture was refluxed for about 1 hour. The acetonitrile solution was concentrated in vacuo, and methylene chloride was added. A white powder was isolated in 60% yield. Anal. Calculated for methanol, 17° C.) (all are broad, featureless resonances): 6.63 (4H), 2.40(4H), 1.64 (4H), −0.93 (4H), −3.30 (4H), −9.08 (4H), −9.62 (4H), −13.21 (4H). ¹³CNMR (d⁴-methanol, 17° C): 76.4, 84.2 (broad), 88.6.

The hydrolysis of m⁷GpppG was monitored by reverse-phase HPLC chromatography using a Beckman System Gold™ apparatus equipped with a Model 126 dual pump module and a Model 168 diode array detector (Beckman Instruments, Palo Alto, Calif.). Separation was achieved with a Beckman Ultrasphere ODS-3 column (4.6 mm i.d.× 250 mm long). A linear gradient solvent system was employed for the separation: Solvent A=60 mM ammonium dihydrogen phosphate/5 mM tetrabutylammonium phosphate 0–50%; Solvent B=95% methanol/5 mM tetrabutylammonium phosphate; 0–50% Solvent B, 0–20 minutes; flow rate=1.0 mL/min. Peaks corresponding to m⁷GpppG and its hydrolysis products were monitored by absorbance at 254 nm. According to these conditions, the following retention times were determined for the specified known standards:

| | |
|---|---|
| m⁷GMP | 6.5 min. |
| GMP | 10.5 min. |
| m⁷GpppG | 14.7 min. |
| GDP | 15.2 min. |
| GTP | 18.14 min. |

Hydrolysis reactions contained m⁷GpppG (55 mM) and the test catalyst in 20 mM HEPES buffer (pH 7.5) (final volume=300 μL). Samples were incubated in a circulating water bath at 37° C. At appropriate time intervals, aliquots (100 μL) were removed, rapidly frozen in dry ice/ethanol, and stored at −20° C. Then, individual samples were removed from the freezer and analyzed immediately by reverse-phase HPLC as described above. Hydrolysis was determined as a reduction in the peak area corresponding to m⁷GpppG and the appearance of new peaks corresponding to hydrolysis products. To determine the half-life for hydrolysis ($t_{1/2}$), a semi-logarithmic plot was made of the fraction of m⁷GpppG degraded versus time. A linear least-squares fit was then applied to the data and the $t_{1/2}$ was determined at the point where log(0.5)=−0.301. According to this analysis, the following data was obtained:

| Catalyst | Concentration | $t_{1/2}$ |
|---|---|---|
| Ethylenediamine | 200 mM | 78 hours |
| Eu[S-THP] | 0.5 mM | 60 hours |
| Eu[THED] | 0.5 mM | 0.11 hours |

The data indicate that the rate at which chelated europium catalysts can cleave m⁷GpppG can be modified by at least four orders of magnitude with slight modifications to the ligands surrounding the metal.

EXAMPLE 2

Cleavage of the m⁷GpppG Cap Structure in an Oligoribonucleotide Target Sequence by a Metal Complex Containing Hydrolytic Catalyst The present example demonstrates that a Lewis acid hydrolytic catalyst may successfully be used to cleave a 5'-cap structure situated at the 5'-terminus of a target oligoribonucleotide sequence. In particular, the ability of Eu[THED]$^{3+}$ to hydrolyze 5'-capped RNA was established using a 3'-radiolabeled, 5'-capped RNA transcript.

A target oligonucleotide transcript having the following sequence was used (SEQ ID NO:1):

5'-$^{7Me}$GpppGGAGACCCAAGCUUGUCGACUC-
   GAGUGCAGGAGCUAAG-3'

Preparation of DNA Template for In Vitro Transcription

Because short transcripts (25–500 nt) such as that shown above are not transcribed as efficiently as longer ones (more transcription initiation events are required to synthesize a given mass of RNA than are required for a long transcript), a relatively high concentration of template DNA (~200 nM) in the transcription reaction is required. Thus, typical large plasmid templates cannot be used directly as the DNA template because too great a mass amount of plasmid would be required to achieve optimum concentration of the desired transcript. Therefore, PCR techniques were used in this example to produce a small (110 bp) amplicon containing the T7 promoter and a section downstream of the promoter coding for the transcript described above. This amplicon could then be utilized in the transcription reaction at a high enough molar concentration to achieve efficient transcription.

Plasmid pG1040, containing UCAT inserted into a pRc/CMV vector, was used as the PCR template. UCAT was made from wild-type CAT DNA (Pharmacia) using synthetic DNA primers. The resulting fragment was cloned as a Hind III (5' end), Not I (3' end) fragment into vector pRc/CMV (Invitrogen). The first adenosine of the open reading frame is designated+1. The amino acid changes between wild-type and pG1040 are conservative, as shown below.

pG1040 (UCAT) 5' untranslated regions and amino terminus:

```
                Wild-type CAT (SEQ ID NO:2):
5'                          +1
                            Met Glu Lys Lys Ile Ser Gly
uuu uca gga gcu aag gaa gcu aaa aug gag aaa aaa auc acu gga
                3'
Tyr Thr Thr
uau acc acc pG1040, UCAT (SEQ ID NO:3):
5'                          +1
                            Met Glu Lys Lys Ile Ser Gly
agu gca gga gcu aag gaa gcu acc aug gag aag aag auc acu gga
                3'
Tyr Thr Thr
uau acc acc
```

The region amplified by PCR is shown below (SEQ ID NO:4). The sequence is shown as the mRNA. In this depiction, the underlined segments are the sequences complementary to the PCR primers, the bolded segment is the T7 promoter, and the AUG start codon is shown in lower case type.

GCAGAGCUCUCUGGCUAACUAGAGAACCCACUG-
CUUAACU
+1→
GGCUUAUCGAAAUUAAUACGACUCAC-
UAUAGGGAGACCCA
AGCUUGUCGACUCG
AGUGCAGGAGCUAAGGAAGCUACCau
gGAGAAGAAGAUCACUGGAUAUACCAC-
CGUUGAUAUAUCC
CAAUCGCAUCG

The PCR procedure produced a single 110 bp band which was visualized on an EtBr-stained agarose gel. The PCR amplicon was purified from an agarose gel using low melt agarose and GELase™ which digests long-chain polysaccharides in molten agarose.

In Vitro Transcription Reaction

5'-capped RNA was made from the above amplicon using a T7 MEGAshortscript™ transcription kit (Ambion). 5'-capped transcripts were synthesized in a 20 μL reaction volume containing transcription buffer, T7 RNA polymerase, 7.5 mM rNTPs (except rGTP), 1.9 mM rGTP, 7.5 mM $^{7Me}$GpppG and 200 nM DNA amplicon template. For synthesis of uncapped RNA, the capping dinucleotide was omitted from the reaction and rGTP concentration was increased to 7.5 mM. Reaction mixtures were incubated four hours at 37° C. After the transcription reaction was complete, template DNA was digested with 1 U DNase for 15 minutes at 37° C. Transcripts were purified from unincorporated nucleotides and truncated message by PAGE. The transcripts were visualized by UV back shadowing, and the RNA in the excised gel bands was purified using an RNaid™ kit (Bio 101) which is designed specifically for purification of RNA from polyacrylamide gels. As expected, the product of the 5'-capped RNA reaction contained a band that ran one base slower than the uncapped transcript on a 15% gel.

3'-End-Labeling of Transcripts

Transcripts were 3' end-labeled with $^{32}p$ cordycepin triphosphate using terminal transferase. This enzyme prefers DNA as a substrate, but limited labeling of RNA can be achieved with the use of $Co^{++}$. As expected, 3'-end-labeling occurred, but the extent of labeling was low.

Cleavage of 5'-Capped RNA by $Eu[THED]^{3+}$

After preparing 3'-end-labeled, 5'-capped RNA, the ability of $Eu[THED]^{3+}$ to cleave (or "decapitate") the cap structure of the RNA was tested. The reaction conditions were as follows: 1 mM $Eu[THED]^{3+}$, 75 μM capped RNA target (~3 mM with respect to phosphate bonds), 20 mM Tris-HCl, pH 7.0, 100 mM NaCl and 0.2% SDS. A second set of samples further contained 100 μM of an 18-mer DNA oligomer which was complementary to the sequence immediately adjacent to the 5'-cap. The results for both data sets suggest that $Eu[THED]^{3+}$ preferentially hydrolyzes the 5'-cap of RNA over backbone diester bonds, with a $T_{1/2}$ of about three hours for cap cleavage. There was no evidence of backbone cleavage in either data set, presumably because the RNA strand was in phosphate bond excess over catalyst. The results are shown below:

| Time (min) | | counts/area | |
| --- | --- | --- | --- |
| | | ssRNA | Hybrid |
| 0 | Capped | 3266 | 3975 |
| | Decapitated | 1130 | 1031 |
| 15 | Capped | ND | 4073 |
| | Decapitated | ND | 923 |
| 30 | Capped | 3481 | 4070 |
| | Decapitated | 1736 | 1073 |
| 60 | Capped | ND | 3315 |
| | Decapitated | ND | 1583 |
| 120 | Capped | 2232 | 3509 |
| | Decapitated | 2195 | 1946 |
| 180 | Capped | 1982 | 2658 |
| | Decapitated | 1949 | 1934 |
| Buffer | Capped | 3451 | 3786 |
| Control | Decapitated | 835 | 577 |

The results, which are depicted in FIG. 1, clearly demonstrate that $Eu[THED]^{3+}$ is capable of specifically cleaving the 5'-cap of an oligoribonucleotide substrate. Furthermore, by conjugating a Lewis acid cleavage moiety such as $Eu[THED]^{3+}$ to a target-complementary oligonucleoside sequence, as for example by using a 3'-end linker as taught hereinabove, the resulting cleavage compound may be used to achieve target-specific cleavage of the cap structure of a desired RNA substrate.

EXAMPLE 3

Preparation of a Chelate Conjugar Suitable for Covalent Coupling Onto an Oligonucleotide A preferred embodiment of a chelate conjugar for use in the present invention is compound 1, which may be synthesized as described in the scheme below. This compound may be conjugated with a target-complementary oligonucleoside, and complexed with a suitable Lewis acid, particularly a metal ion such as europium, to afford a cleavage moiety as taught herein.

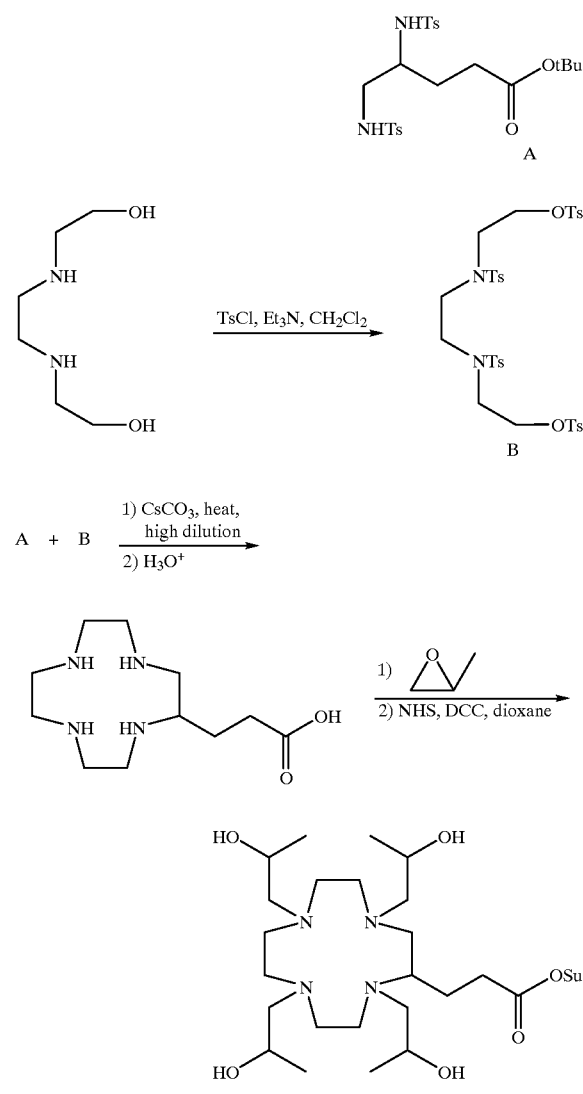

EXAMPLE 4

Preparation of an Oligonucleoside Containing a Primary Amine at the 3'-terminus Suitable for Covalent Attachment of the Chelate Conjugar Compound 1

Attachment of chelate conjugar 1 to an oligonucleoside may be achieved by inclusion of a primary aliphatic amino moiety located at or near the 3'-end of the oligonucleoside. This can be accomplished by, for example, use of a non-nucleotide based linker group as described in PCT Publication No. WO 92/02532 (incorporated herein by reference), or by the synthetic scheme outlined below.

Method of modification of probe for conjugar chelate attachment

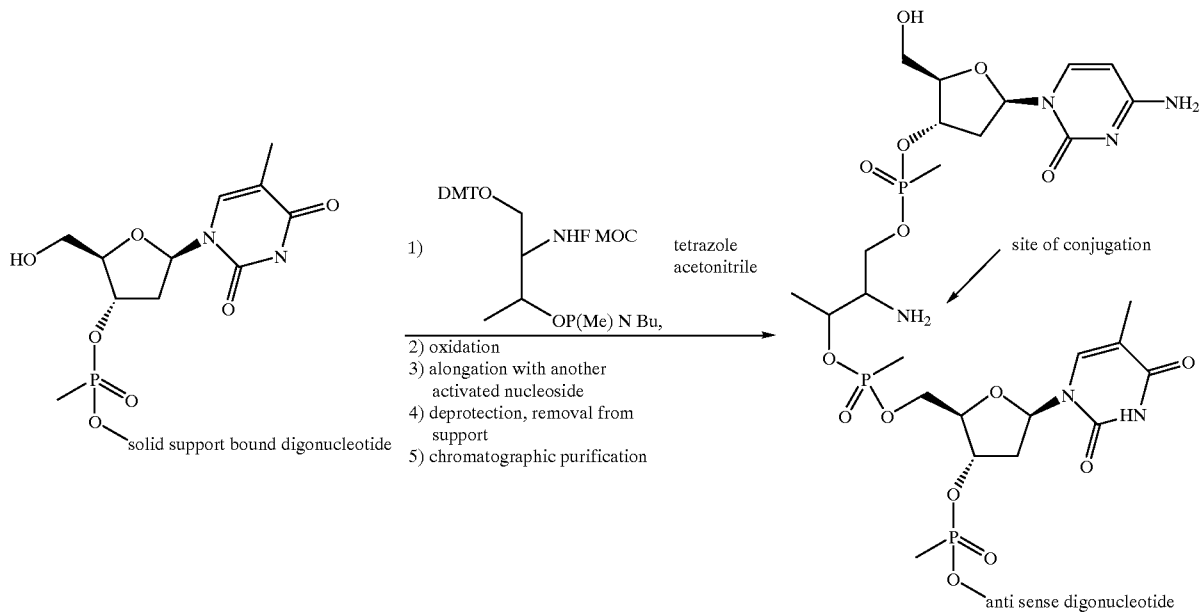

EXAMPLE 5

Attachment of Chelate Conjugar Compound to an Oligonucleoside

A preferred oligonucleoside sequence for the 5'-capped target described in Example 2 is shown below: (SEQ ID NO:5):

3'-N-(L)-CCU CUG GGU UCG AAC AGC UGA-5'    Oligo 1 where N is any of the four standard nucleotide bases, most preferably one that is not complementary to the target 5'-capped RNA sequence (for example, thymidine); and (L) refers to a primary amine attachment point, as for example the non-nucleotide based linker described in the preceding example.

Conjugar compound 1 can be covalently attached to the Oligo 1 according to the following procedure, which is intended only as one possible route. One skilled in the art will recognize in view of the present teachings that other procedures would also avail themselves to the same type of covalent product.

Compound 1 is dissolved in anhydrous DMSO to give a 50–70 mM stock solution. Next, about 10–100 $OD_{260}$ units of Oligo 1 is suspended in about 400 μL of reaction buffer (100 mM HEPES, pH, 8.0, 50% DMSO) and about 50 μL of Compound 1 (50 mM in DMSO) is added. The resulting mixture is then incubated at 37° C. for about 30–45 minutes. Then, 1 mL of absolute ethanol is added and the contents are mixed to precipitate the modified oligonucleoside. The sample is chilled at −20° C. for at least 5 hours and then spun in a microcentrifuge for at least 10 minutes at 4° C. The resulting modified oligomer can be further purified to remove unmodified oligomer by a variety of methods, for example, HPLC chromatography. To identify the appropriate conditions for HPLC chromatography, analytical samples of the crude product can be injected onto a variety of different columns (for example, C18 reverse-phase, silica based normal phase, etc.). Preferable elution conditions for a reverse-phase column involve a dual-gradient system composed of two different buffers, one containing a water miscible organic co-solvent (for example: Buffer A=100 mM triethylammonium acetate (pH 7); Buffer B=50% acetonitrile in 100 mM triethylammonium acetate (pH 7)). In the case of a reverse-phase HPLC column separation, elution conditions can be tested ranging from 0–100% Buffer B or any intermediate gradient within this range. If it is determined that the product oligomer elutes at a different retention time compared to the unmodified oligomer, then this method can be scaled up to purify the desired product oligomer. Confirmation that the chelate conjugar has been attached to the oligomer can be obtained, for example, by electrospray mass spectrometry.

EXAMPLE 6

Preparation of Oligoribonucleosides

The oligoribonucleosides described in the preceding examples may be synthesized using procedures such as those of the present example.

The oligoribonucleosides are synthesized using 5'-O-dimethoxytrityl-2'-O-tert-butyldimethylsilyl-3'-O-N,N-diisopropyl-β-cyanoethylphosphoramidite nucleosides (purchased from either Milligen or Peninsula Laboratories). The syntheses are done on a 1 μmole scale with a Milligen 8750 automated DNA synthesizer using standard Milligen phosphoramidite procedures with the exception that the coupling times are extended to 12 minutes to allow adequate time for the more sterically hindered 2'-O-tert-butyldimethylsilyl RNA monomers to react. The syntheses are begun on control pore glass bound 2'-O-tert-butyldimethylsilyl ribonucleosides purchased from Peninsula Laboratories. All other oligonucleoside synthesis reagents are as described in Milligen's standard protocols.

After synthesis, the oligonucleosides are handled under sterile, RNase-free conditions. Water is sterilized by overnight treatment with 0.5% diethylpyrocarbonate followed by autoclaving. All glassware is baked for at least 4 hours at 300° C.

The oligonucleosides are deprotected and cleaved from support by first treating the support-bound oligonucleoside with 3:1 ammonium hydrazide/ethanol for 15 hours at 55° C. The supernatant, which contains the oligonucleoside, is then decanted and evaporated to dryness. The resultant residue is then treated with 0.6 mL of 1 M tetra-butylammonium fluoride in tetrahydrofuran (which contains 5% or less water) for 24 hours at room temperature. The reaction is quenched by the addition of 0.6 mL of aqueous 2 M triethylammonium acetate, pH 7. Desalting of the reaction mixture is accomplished by passing the solution through a Bio-Rad 10DG column using sterile water. The desalted oligonucleoside is then dried.

Purification of the oligoribonucleosides is done by polyacrylamide gel electro-phoresis (PAGE) containing 15% 19:1 polyacrylamide/bis-acrylamide and 7 M urea using standard procedures (see, Maniatis, T. et al., *Molecular Cloning: A Laboratory Manual*, pages 184–185 (Cold Spring Harbor 1982)). The gels are 20 cm wide by 40 cm long and 6 mm in width. The oligoribonucleotides (60 OD Units) are dissolved in 200 μL of water containing 1.25% bromophenol blue and loaded onto the gel. The gels are run overnight at 300 V. The product bands are visualized by UV backshadowing, excised, and the product eluted with 0.5 M sodium acetate overnight. The product is desalted using a Waters C18 Sep-Pak cartridge with the manufacturer supplied protocol. The product is then kinased and analyzed by PAGE.

It is evident from the results reported herein that the described oligonucleoside cleavage compounds should be effective agents for reducing or preventing expression of undesired nucleic acid. By controlling the expression of target nucleic acid, various diseases and conditions may be treated.

All publications and patent documents cited in this specification are incorporated herein by reference as if each individual document were specifically and individually indicated to be incorporated by reference.

Although the present invention has been described in some detail by way of illustration and example for purposes of clarity of understanding, it will be readily apparent to those of ordinary skill in the art in light of the teachings of this invention that various changes and modifications may be made thereto without departing from the spirit or scope of the claims. Therefore, the foregoing description should not be construed to limit the scope of the present invention, which is set forth in the appended claims.

What is claimed is:

1. An oligonucleoside cleavage compound for hybridizing to the 5'-terminal region of a target mRNA nucleic acid strand and effecting cleavage of the 5'-cap structure of the target strand, comprising an oligonucleoside sequence that is substantially complementary to the 5'-terminal region of the target nucleic acid strand, and a cleavage moiety situated at a position in the cleavage compound that is proximate to the 5'-cap structure of the target strand upon hybridization, such that the cleavage moiety is capable of effecting cleavage of the 5'-cap structure of the target strand, and wherein the cleavage moiety comprises a lanthanide ion.

2. The oligonucleoside cleavage compound of claim 1 wherein the cleavage moiety comprises a complexed lanthanide ion.

3. The oligonucleoside cleavage compound of claim 2 wherein the complexed lanthanide ion comprises europium (III).

4. The oligonucleoside cleavage compound of claim 2 wherein the cleavage moiety comprises a macrocyclic complexing agent.

5. The oligonucleoside cleavage compound of claim 3 wherein the cleavage moiety comprises a macrocyclic complexing agent.

6. The oligonucleoside cleavage compound of claim 4 wherein the complexing agent is 1,4,7,10-tetrakis (2-hydroxyethyl)-1,4,7,10-tetraazacyclododecane.

7. The oligonucleoside cleavage compound of claim 5 wherein the complexing agent is 1,4,7,10-tetrakis (2-hydroxyethyl)-1,4,7,10-tetraazacyclododecane.

8. A method for inhibiting production of a selected protein in a cell, comprising administering to the cell the oligonucleoside cleavage compound of claim 2, wherein the target mRNA nucleic acid strand codes for the selected protein.

9. A method for inhibiting production of a selected protein in a cell, comprising administering to the cell the oligonucleoside cleavage compound of claim 3, wherein the target mRNA nucleic acid strand codes for the selected protein.

10. A method for inhibiting production of a selected protein in a cell, comprising administering to the cell the oligonucleoside cleavage compound of claim 4, wherein the target mRNA nucleic acid strand codes for the selected protein.

11. A method for inhibiting production of a selected protein in a cell, comprising administering to the cell the oligonucleoside cleavage compound of claim 5, wherein the target mRNA nucleic acid strand codes for the selected protein.

12. A method for inhibiting production of a selected protein in a cell, comprising administering to the cell the oligonucleoside cleavage compound of claim 6, wherein the target mRNA nucleic acid strand codes for the selected protein.

13. A method for inhibiting production of a selected protein in a cell, comprising administering to the cell the oligonucleoside cleavage compound of claim 7, wherein the target mRNA nucleic acid strand codes for the selected protein.

14. A method for inhibiting production of a selected protein in a cell, comprising administering to the cell the oligonucleoside cleavage compound of claim 1, wherein the target mRNA nucleic acid strand codes for the selected protein.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: mRNA (iii) HYPOTHETICAL: no (iv) ANTI-SENSE: no (ix) FEATURE:
      (A) NAME/KEY: target mRNA transcript (5'-cap portion)
      (D) OTHER INFORMATION: transcribed from SEQ ID
          NO:4 amplicon (xi) SEQUENCE DESCRIPTION: SEQ ID NO:1:

GGGAGACCCA AGCUUGUCGA CUCGAGUGCA GGAGCUAAG                39

(2) INFORMATION FOR SEQ ID NO:2:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (ii) MOLECULE TYPE: mRNA (iii) HYPOTHETICAL: no (iv) ANTI-SENSE: no (ix) FEATURE:
      (A) NAME/KEY: wild-type CAT gene portion (as mRNA)

(xi) SEQUENCE DESCRIPTION: SEQ ID NO:2:

```
UUUUCAGGAG CUAAGGAAGC UAAA AUG GAG AAA AAA AUC ACU GGA UAU ACC        51
                          Met Glu Lys Lys Ile Ser Gly Tyr Thr
                          1                 5

ACC                                                                    54
Thr
10
```

(2) INFORMATION FOR SEQ ID NO:3:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: no (ix) FEATURE:
        (A) NAME/KEY: pG1040 insert (as mRNA)

(xi) SEQUENCE DESCRIPTION: SEQ ID NO:3:

```
AGUGCAGGAG CUAAGGAAGC UACC AUG GAG AAG AAG AUC ACU GGA UAU ACC        51
                          Met Glu Lys Lys Ile Ser Gly Tyr Thr
                          1                 5

ACC                                                                    54
Thr
10
```

(2) INFORMATION FOR SEQ ID NO:4:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: no (ix) FEATURE:
        (A) NAME/KEY: PCR amplicon from pG1040 template
            (as mRNA)
        (D) OTHER INFORMATION: template for SEQ ID NO:1

(xi) SEQUENCE DESCRIPTION: SEQ ID NO:4:

```
GCAGAGCUCU CUGGCUAACU AGAGAACCCA CUGCUUAACU GGCUUAUCGA AAUUAAUACG        60

ACUCACUAUA GGGAGACCCA AGCUUGUCGA CUCGAGUGCA GGAGCUAAGG AAGCUACC         118

AUG GAG AAG AAG AUC ACU GGA UAU ACC ACC GUU GAU AUA UCC CAA UCG CAU    171
Met Glu Lys Lys Ile Ser Gly Tyr Thr Thr Val Asp Ile Ser Gln Ser His
1                 5                 10                  15

CG
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued

```
    (ii) MOLECULE TYPE:  other nucleic acid (iii) HYPOTHETICAL: no (iv) ANTI-SENSE: yes (ix) FEATURE:
         (A) NAME/KEY: antisense oligo 1
         (C) IDENTIFICATION METHOD:  complementarity to SEQ ID NO:1
         (D) OTHER INFORMATION: for attachment to chelate conjugar
             compound (xi) SEQUENCE DESCRIPTION: SEQ ID NO:5:

AGUCGACAAG CUUGGGUCUC CN                                                    22
```